United States Patent
Zenoni et al.

(10) Patent No.: US 6,583,291 B2
(45) Date of Patent: Jun. 24, 2003

(54) PROCESS FOR OBTAINING COMPOUNDS USABLE IN THE PRODUCTION OF CEFOTETAN, AND NEW COMPOUNDS OBTAINED THEREBY

(75) Inventors: Maurizio Zenoni, Paullo (IT); Alessandro Donadelli, Casalpusterlengo (IT); Marco Silvagni, Segrate (IT)

(73) Assignee: ACS Dobfar S.p.A., Tribiano (IT)

( * ) Notice: Subject to any disclaimer, the term of this patent is extended or adjusted under 35 U.S.C. 154(b) by 0 days.

(21) Appl. No.: 10/123,151

(22) Filed: Apr. 17, 2002

(65) Prior Publication Data

US 2002/0169327 A1 Nov. 14, 2002

(30) Foreign Application Priority Data

May 10, 2001 (IT) ..................... MI2001A0964

(51) Int. Cl.⁷ ............................. C07D 275/03
(52) U.S. Cl. ....................................... 548/213
(58) Field of Search ......................... 548/213

(56) References Cited

U.S. PATENT DOCUMENTS 3,230,229 A    1/1966  Hatchard
3,887,352 A  * 6/1975  Lewis et al. ................. 504/156
4,263,432 A    4/1981  Iwanami et al.
4,508,908 A  * 4/1985  Virgilio et al. .............. 548/213

OTHER PUBLICATIONS

M. Iwanami, et al., Chem. Pharm. Bull., vol. 28, No. 9., pp. 2629–2636, XP–002209216, "Synthesis of New Cephamycin Derivatives and a Novel Rearrangement Between Isothiazolethioacetamides and 1,3–Dithietanecarboxamides", 1980.

* cited by examiner

Primary Examiner—Mark L. Berch
(74) Attorney, Agent, or Firm—Oblon, Spivak, McClelland, Maier & Neustadt, P.C.

(57) ABSTRACT

A safe and economical process for obtaining salts of 4-carboxy-3-hydroxy-5-mercapto-isothiazole. This process comprises refluxing a disodium or dipotassium salt of 3-hydroxy-5-mercapto-4-isothiazole carbonitrile in an aqueous solution of sodium or potassium hydroxide to produce the desired salt. The desired salt may be precipitated out of solution by adjusting the pH downward to a minimum value of about pH 8. Compounds produced by this process may be used for producing semi-synthetic cephalosporins.

11 Claims, No Drawings

PROCESS FOR OBTAINING COMPOUNDS USABLE IN THE PRODUCTION OF CEFOTETAN, AND NEW COMPOUNDS OBTAINED THEREBY

The present invention relates both to a process for obtaining sodium or potassium salts of 4-carboxy-3-hydroxy-5-mercapto-isothiazole which are compounds usable in the production of Cefotetan, and to new compounds obtained by the process.

Cefotetan is a semi-synthetic injectable cephalosporin of formula

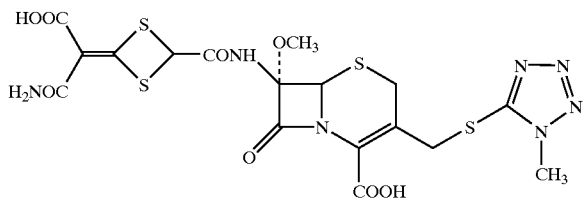

(I)

According to the method described in U.S. Pat. No. 4,263,432 and in Chem. Pharm. Bull. 28, 2629–2636 (1980), Cefotetan is obtained from 7 á-(4-carboxy-3-hydroxyisothiazol-5-yl)thioacetamido-7 á-methoxy-3-(1-methyltetrazol-5-yl)thiomethyl-Ä$^3$-cephem-4-carboxylic acid of formula

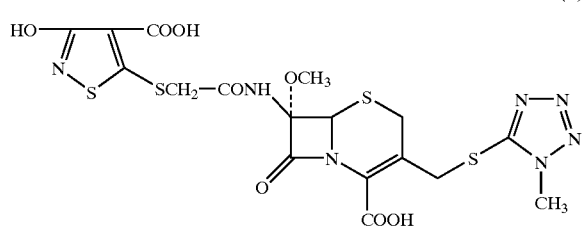

(II)

which is itself prepared by reacting 7 á-bromoacetamido-7á-methoxy-3-(1-methyltetrazol-5-yl) thiomethyl-Δ$^3$-cephem-4-carboxylic acid with a trisodium 4-carboxy-3-hydroxy-5-mercapto-isothiazole of formula

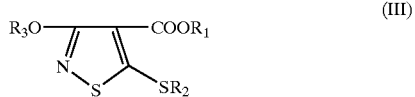

(III)

where $R_1=R_2=R_3=Na$.

The reaction mixture is adjusted to pH 8.0 with dilute HCl and a precipitate of the compound of formula (I) is obtained. The trisodium 4-carboxy-3-hydroxy-5-mercapto-isothiazole of formula (III) in which $R_1=R_2=R_3=Na$ is an essential intermediate (according to the known art) in the preparation of Cefotetan.

The aforementioned literature also describes the single method currently used to prepare the trisodium 4-carboxy-3-hydroxy-5-mercapto-isothiazole of formula (III) in which $R_1=R_2=R_3=Na$; this method is very lengthy and impractical and especially requires the use of metal sodium and liquid ammonia, as explained in detail on page 2633 of the aforementioned edition of Chem. Pharm. Bull.

An object of the present invention is therefore to provide, for the preparation of compounds of formula (III), a method which is economically very advantageous compared with the known method, and avoids the use of dangerous substances such as metal sodium and ammonia.

The invention hence relates to a process for obtaining 4-carboxy-3-hydroxy-5-mercapto-isothiazole salts of formula

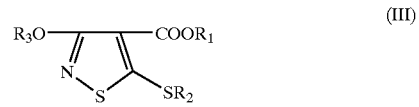

(III)

in which $R_1=R_2=R_3=Na$ or K; $R_1=Na$ or K and $R_2=R_3=H$; or $R_1=R_2=Na$ or K and $R_3=H$, wherein the disodium or dipotassium salt of 3-hydroxy-5-mercapto-4-isothiazole carbonitrile is refluxed in an aqueous solution of sodium hydroxide or potassium hydroxide in a quantity between 3 and 6 equivalents for a time period of at least 15 h, to give an aqueous solution containing the trisodium or respectively tripotassium salt of 4-carboxy-3-hydroxy-5-mercapto-isothiazole (III) in which $R_1=R_2=R_3=Na$ or K, the salt being precipitated from this solution when the solution pH is corrected to a minimum value of about 8 by adding HCl.

In particular the pH of said aqueous solution is adjusted between 8.0 and 8.5 to precipitate the compound of formula (III) in which $R_1=Na$ or K and $R_2=R_3=H$.

The disodium or dipotassium salt of 3-hydroxy-5-mercapto-4-isothiazole carbonitrile is easily produced with a yield of 97% by reacting the disodium or dipotassium salt of dicyano-1,1-ethylene-dithiol with 30% hydrogen peroxide, as described in U.S. Pat. No. 3,230,229.

The salts of the compound of formula (III) in which $R_1=Na$ or K and $R_2=R_3=H$ are new compounds and also form a subject of the present invention. It is important to note that if Cefotetan is to be produced using the tri-sodium or tri-potassium salt of the compound of formula (III) the pH of the solution of this salt (a strongly basic solution) must be considerably lowered (to about pH 8.5) by large additions of concentrated HCl.

The solutions of the mono-salt and di-salt according to the invention are also of basic pH but much lower, so that these solutions can be used directly without adding HCl or only with a minimum addition of HCl, for direct industrial use in the production of Cefotetan.

In order to clarify the understanding of the characteristics of the present invention, some non-limiting examples are given hereinafter.

EXAMPLE 1

Compound of Formula (III) in Which $R_1=Na$ and $R_2=R_3=H$

The disodium salt of 3-hydroxy-5-mercapto-4-isothiazole carbonitrile (162.53 g, 0.8 mol) is dissolved in water (620 ml) and solid sodium hydroxide (192 g, 4.8 mol) is added to the solution.

The solution is kept under reflux for 16 h and is then cooled to ambient temperature; in this manner an aqueous solution (of pH 14) of the compound (III) in which $R_1=R_2=R_3=Na$ is obtained. Water (380 ml) is added to this solution, the temperature is lowered to 0° C. and the pH is corrected to 8.4 by adding concentrated HCl. The mixture is stirred for 1 h to obtain a precipitate (consisting of the compound indicated in the title) which is filtered off, washed with ethanol and dried at 35° C. under reduced pressure for 8 h.

Yield: 157.4 g white powder.

HPLC: 80%; K.F. 19.6%; m.p. 160° C. with decomposition.

$^{13}$C-N.M.R. (DMSO-$d_6$) (300 MHz): 188.94 ppm; 172.02 ppm; 171.26 ppm; 113.11 ppm.

The compound indicated in the title can be dissolved in water, to give a solution having a pH of about 8.5.

EXAMPLE 2

Compound of Formula (III) in Which $R_1$=Na and $R_2$=$R_3$=H in solution for Cefotetan Synthesis The disodium salt of 3-hydroxy-5-mercapto-4-isothiazole carbonitrile (86.7 g, 0.43 mol) is dissolved in water (180 ml) and solid sodium hydroxide (51.5 g, 1.29 mol) is added to the solution.

The solution is kept under reflux for 16 h and is then cooled to ambient temperature. Water (380 ml) is added, the temperature is lowered to 10° C. and the pH is corrected to 8.5 by adding concentrated HCl. The solution obtained is used directly for preparing Cefotetan.

EXAMPLE 3

Compound of Formula (III) in Which $R_1$=K and $R_2$=$R_3$=H in Solution for Cefotetan Synthesis The dipotassium salt of 3-hydroxy-5-mercapto-4-isothiazole carbonitrile (62.5 g, 0.27 mol) is dissolved in water (238 ml) and solid potassium hydroxide (90.9 g, 1.62 mol) is added to the solution.

The solution is kept under reflux for 18 h and is then cooled to ambient temperature to give a solution the pH of which is corrected to pH 8.5 by adding concentrated HCl. The temperature is lowered to 10° C. and the solution is used directly for preparing Cefotetan.

We claim:

1. A process for obtaining a mono-, di- and/or tripotassium salt of 4-carboxy-3-hydroxy-5-mercapto-isothiazole or a mono-, di- and/or tri-sodium salt of 4-carboxy-3-hydroxy-5-mercapto-isothiazole comprising formula (III):

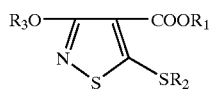

(III)

wherein
$R_1$, $R_2$ and $R_3$ are Na, or $R_1$, $R_2$ and $R_3$ are K;
$R_1$ and $R_2$ are Na and $R_3$ is H, or $R_1$ and $R_2$ are K and $R_3$ is H; or
$R_1$ is Na and $R_2$ and $R_3$ are H, or $R_1$ is K and $R_2$ and $R_3$ are H; comprising:
refluxing the disodium or dipotassium salt of 3-hydroxy-5-mercapto-4-isothiazole carbonitrile in an aqueous solution of between 3 to 6 equivalents of sodium hydroxide or potassium hydroxide for a time period of at least 15 h, to give an aqueous solution comprising the trisodium or respectively tripotassium salt of 4-carboxy-3-hydroxy-5-mercapto-isothiazole (III) in which $R_1$, $R_2$ and $R_3$ are each Na or each K, and
precipitating the salt from this solution by lowering the pH, by adding sufficient HCl to cause precipitation, wherein the pH is not lowered beyond pH 8.

2. The process of claim 1, wherein the pH of said aqueous solution is adjusted to between 8.0 and 8.5 to precipitate the compound of formula (III) in which $R_1$=Na or K and $R_2$=$R_3$ H.

3. A salt of 4-carboxy-3-hydroxy-5-mercapto-isothiazole of formula

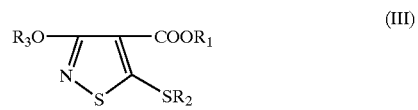

(III)

in which $R_1$=Na or K and $R_2$=$R_3$=H.

4. The salt of claim 3, wherein $R_1$ is sodium.

5. The salt of claim 3, wherein $R_1$ is potassium.

6. The process of claim 1 that produces a monosodium salt.

7. The process of claim 1 that produces a monopotassium salt.

8. The process of claim 1 that produces disodium salt.

9. The process of claim 1 that produces dipotassium salt.

10. The process of claim 1 that produces a trisodium salt.

11. The process of claim 1 that produces tripotassium salt.

* * * * *